US008652503B2

(12) United States Patent
Wironen et al.

(10) Patent No.: US 8,652,503 B2
(45) Date of Patent: Feb. 18, 2014

(54) BONE PASTE

(75) Inventors: John F. Wironen, Topsham, ME (US); Jamie M. Grooms, Gainesville, FL (US)

(73) Assignees: University of Florida Research Foundation, Inc., Gainesville, FL (US); Regeneration Technologies, Inc., Alachua, FL (US)

( * ) Notice: Subject to any disclaimer, the term of this patent is extended or adjusted under 35 U.S.C. 154(b) by 2169 days.

(21) Appl. No.: 11/152,548

(22) Filed: Jun. 14, 2005

(65) Prior Publication Data
US 2007/0003593 A1 Jan. 4, 2007

Related U.S. Application Data

(63) Continuation of application No. 08/816,079, filed on Mar. 13, 1997, now abandoned.

(51) Int. Cl.
*A61F 2/00* (2006.01)
*A61F 13/00* (2006.01)
*A61F 2/28* (2006.01)

(52) U.S. Cl.
USPC ........ 424/423; 424/422; 523/115; 623/23.61; 623/23.63

(58) Field of Classification Search
USPC ............... 424/423, 422; 523/115; 623/23.61, 623/23.63
See application file for complete search history.

(56) References Cited

U.S. PATENT DOCUMENTS

| 3,034,852 A | 4/1960 | Nishihara |
| 4,191,747 A | 3/1980 | Scheicher |
| 4,294,753 A | 10/1981 | Urist |
| 4,394,370 A | 7/1983 | Jefferies |
| 4,440,750 A | 4/1984 | Glowacki et al. |
| 4,472,840 A | 9/1984 | Jefferies |
| 4,587,268 A | 5/1986 | Pfirrman |
| 4,678,470 A | 7/1987 | Nashef et al. |
| 4,931,546 A | 6/1990 | Tardy et al. |
| 5,073,373 A | 12/1991 | O'Leary et al. |
| 5,171,574 A | 12/1992 | Kuberasampath et al. |
| 5,236,456 A | 8/1993 | O'Leary et al. |
| 5,284,655 A | 2/1994 | Bogdansky et al. |
| 5,290,558 A | 3/1994 | O'Leary et al. |
| 5,292,349 A | 3/1994 | Foresti |
| 5,314,476 A | 5/1994 | Prewett et al. |
| 5,356,629 A | 10/1994 | Sander et al. |
| 5,405,390 A | 4/1995 | O'Leary et al. |
| 5,422,340 A | 6/1995 | Ammann et al. |
| 5,484,601 A | 1/1996 | O'Leary et al. |
| 5,503,558 A | 4/1996 | Clokie |
| 5,510,396 A | 4/1996 | Prewett et al. |
| 5,531,791 A | 7/1996 | Wolfinbarger, Jr. |
| 5,707,962 A | 1/1998 | Chen et al. |
| 5,776,193 A | 7/1998 | Kwan et al. |
| 7,824,702 B2 * | 11/2010 | Wironen et al. ............. 424/423 |

FOREIGN PATENT DOCUMENTS

| DE | 4 216 496 A1 | 11/1993 |
| EP | 0 147 021 A1 | 3/1985 |
| EP | 0 329 239 A3 | 8/1989 |
| EP | 0 530 804 A1 | 3/1993 |
| JP | 63 181 770 | 7/1988 |
| JP | 1 032 371 | 2/1989 |
| JP | 1 288 269 | 11/1989 |
| JP | 5 123 390 | 5/1993 |
| JP | 5 277 174 | 10/1993 |
| WO | WO 89/04646 | 6/1989 |
| WO | WO 92/13565 | 8/1992 |
| WO | WO 96/39203 | 12/1996 |

OTHER PUBLICATIONS

Bergman, S. et al., "Bone in-fill of non-healing Calvarial defects using particulate Bioglass® and autogenous bone," *Bioceramics*, pp. 17-21, vol. 8.

Blumenthal, N. et al., "The use of collagen membrane barriers in conjunction with combined demineralized bone-collagen gel implants in human infrabony defects," *J Petiodontol*, Jun. 1990, pp. 319-327, vol. 61.

Oonishi, H. et al., "Comparative bone formation in several kinds of bioceramic granules," *Bioceramics*, pp. 137-144, vol. 8.

Wheeler D. et al., "Histological analysis of Bioglass®-filled radius defects", *Bioceramics*, pp. 69-73, vol. 8.

Wilson, J. et al., "Bone augmentation using Bioclass particulates in dogs: Pilot study," *Bioceramics*, pp. 139-146, vol. 5.

Bard, "Contigen™ Bard® Collagen Implant Physicians' Circular," *Contigen™ Bard® Collagen Implant Physicians Circular*, Sep. 1989.

Benedict, J.J., "The role of carrier matrices on bone induction in vivo," *Society for Biomaterials*, 1996, Denver, CO.

Bentz, H. et al., "Transforming growth factor-beta2 enhances the osteo-inductive activity of a bovine bone-derived fraction containing bone morphogenetic protein-2 and 3," *Matrix*, 1991, pp. 269-275, vol. 11.

(Continued)

*Primary Examiner* — Kara R McMillian
(74) *Attorney, Agent, or Firm* — Saliwanchik, Lloyd & Eisenschenk

(57) ABSTRACT

A bone paste useful in the orthopedic arts, for example in the repair of non-union fractures, periodontal ridge augmentation, craniofacial surgery, implant fixation, impaction grafting, or any other procedure in which generation of new bone is deemed necessary, is provided by a composition comprising a substantially bioabsorbable osteogenic compound in a gelatin matrix. In various embodiments, the osteogenic compound is selected from (i) demineralized bone matrix (DBM); (ii) bioactive glass ceramic, BIOGLASS®, bioactive ceramic, calcium phosphate ceramic, hydroxyapatite, hydroxyapatite carbonate, corraline hydroxyapatite, calcined bone, tricalcium phosphate, or like material; (iii) bone morphogenetic protein, TGF-β, PDGF, or mixtures thereof, natural or recombinant; and (iv) mixtures of (i)-(iii).

15 Claims, 4 Drawing Sheets

(56) References Cited

OTHER PUBLICATIONS

Bergman, S. et al., "Bone in-fill of non-healing Calvarial defects using particulate Bioglass® and autogenous bone," *Bioceramics*, pp. 17-21, vol. 8, (1995).

Black et al., "The mechanical integrity of healed diaphyseal bone defects grafted with calcium hydroxyapatite/calcium triphosphate ceramic in a new animal model," *Clinical Materials*, 1990, pp. 251-264, vol. 6.

Bloebaum, R. "Human bone ingrowth and materials," *Society for Biomaterials*, 1996, Denver, CO., *J. Arthroplasty*, 1995, pp. 203-211, vol. 8, No. 2, *J. Biol. Mat. Res.*, 1994, pp. 537-544, vol. 28.

Blumenthal, N. et al., "The use of collagen membrane barriers in conjunction with combined demineralized bone-collagen gel implants in human infrabony defects," *J Periodontol*, Jun. 1990, pp. 319-327, vol. 61.

Collagen Corporation, "Introducing Zyplast® Implant: A stable solution to deeper problems," *Zyplast® product information*, 1986.

Collagen Corporation, "Zyderm™ Collagen Implant Physician Package Insert," *Zyderm™ Collagen Implant Physician Package Insert*, May 1981.

Cornell, C., "Initial clinical experience with use of Collagraft™ as a bone graft substitute," *Techniques in Orthopaedics*, 1992, pp. 55-63, vol. 7, No. 2.

Editor(s), "Second-hand bones?," *Lancet*, Dec. 1992, pp. 1443, vol. 340.

Einhorn, T. A., "Enhancement of bone repair using biomaterials," *Society for Biomaterials*, 1996, Denver, CO.

Frenkel, S.R. et al., "Demineralized bone matrix: Enhancement of spinal fusion," *Spine*, 1993, pp. 1634-1639, vol. 18, No. 12.

Glowacki, J. et al., "Application of the biological principle of induced osteogenesis for craniofacial defects," *Lancet*, May 1981, pp. 959-963.

Hardin, C., "Banked bone," *Otolaringologic Clin. N. America*, 1994, pp. 911-925, vol. 27, No. 5.

Kligman, A. et al., "Histologic response to intradermal Zyderm and Zyplast (glutaraldehyde cross-linked) collagen in humans," *J. Dermatol Surg Oncol.*, Apr. 1996, pp. 351-357, vol. 12, No. 4.

Kocialkowski, A. et al., "Clinical experience with a new artificial bone graft: Preliminary results of a prospective study," *Injury*, 1990, pp. 142-144, vol. 21.

Lasa, C. et al., "Delivery of demineralized bone powder by fibrin sealant," *Plastic and Reconstructive Surgery*, Nov. 1995, pp. 1409-1417, vol. 96, No. 6.

Low, S. et al., "An evaluation of Perioglas® for the treatment of infrabony osseous defects," *International J of Periodontic & Restorative Dentistry*, Feb. 1995, Abstract only.

Mehlisch, D. et al., "Histologic evaluation of the bone/graft interface after mandibular augmentation with hydroxylapatite/purified fibrillar collagen composite implants," *Oral Surg Oral Med Oral Pathol*, 1990, pp. 685-692, vol. 70.

Muschler, G. et al., "Evaluation of human bone morphogenetic protein 2 in a canine spinal fusion model," *Clin. Orthopaedics*, Nov. 1994, pp. 229-240, vol. 308.

Nathan, R. et al., "Osteogenesis in rats with an inductive bovine compostite," *J. Orthop Res.*, 1988, pp. 324-334, vol. 6, No. 3.

Oonishi, H. et al., "Comparative bone formation in several kinds of bioceramic granules," *Bioceramics*, pp. 137-144, vol. 8, (1995).

Osteotech, Inc., "The next generation in bone grafting technology," *Grafton® Dermineralized Bone Matrix (DBM) product information*, 1995.

Pompili, A. et al., "Cranioplasty performed with a new osteoconductive, osteoinducing hydroxyapatite-derived material," *J. Neurosurg.*, Aug. 1998, pp. 236-242, vol. 89.

Roberts, E., "Bone tissue interface," *J. Dental Education*, 1988, pp. 804-809, vol. 52, No. 12.

Rutherford et al., "Use of bovine osteogenic protein to promote rapid osseointegration of endosseous dental implants," *Int. J. Oral Maxillofac Implants*, 1992, pp. 297-301, vol. 7.

Scarborough, N., "Bone repair using allografts," *Society for Biomaterials*, 1996.

Senn, N., "On the healing of aseptic bone cavities by implantation of antiseptic decalcified bone," *American J. Med. Sci.* 1889, pp. 219-243, vol. 98, No. 3.

Sperling, L. H., "Introduction to Physical Polymer Science," 1992, John Wiley and Sons, Inc., $2^{nd}$ Ed., New York.

St. John, K. et al., "Response of canine bone to a synthetic bone graft material," *Clinical Materials*, 1992, pp. 49-55.

Stegman, S. et al., "A light and electron microscopic evaluation of Zyderm Collagen and Zyplast implants in aging human facial skin," *Arch Dermatol*, Dec. 1987, pp. 1644-1649, vol. 123.

Strates, B. et al., "Contribution of osteoinductive and osteoconductive properties of demineralized bone matrix to skeletal repair," *European J. Experimental Musculoskeletal Res.*, 1993, pp. 61-67, vol. 2.

Swanker, W. et al., "Use of Gelatinized Bone in Skeletal Trauma," *Am. J. Surg.*, 1952, pp. 332-341, vol. 83.

Urist, M., *Bone morphogenetic protein*, 1992, pp. 70-83, Chapter 7, W.B. Saunders Co., Philadelphia, Pennsylvania.

Urist, M. et al., "Preparation and bioassay of bone morphogenetic protein and polypeptide fragments," *Methods in Enzymology*, 1987, pp. 294-312, vol. 146.

Urist, M. et al., "Purification of bovine bone morphogenetic protein by hydroxyapatite chromatography," *Proc. Nat. Acad. Sci, USA*, 1984, pp. 371-375, vol. 81.

Vrouwenvelder, W. et al., Histological and biochemical evaluation of osteoblasts cultured on bioactive glass, hydroxylapatite, titanium alloy, and stainless steel, *J. Biomedical Materials Res.*, 1993, pp. 465-475, vol. 27.

Walker, et al., "Injectable bioglass as a potential substitute for injectable polytetrafluoroethylene," *J. Urology*, Aug. 1992, pp. 645-647, vol. 148.

Wheeler D. et al., "Histological analysis of Bioglass®-filled radius defects", *Bioceramics*, pp. 69-73, vol. 8, (1995).

Wilson, J. et al., "Bioactive ceramics for periodontal treatment: comparative studies in the Patus monkey," *J. Applied Biomaterials*, 1992, pp. 123-129, vol. 3.

Wilson, J. et al., "Bone augmentation using Bioclass particulates in dogs: Pilot study," *Bioceramics*, pp. 139-146, vol. 5, (1993).

Wilson, J. et al., "Clinical applications of Bioglass® implants," $7^{th}$ *International Symposium on Ceramics in Medicine*, Jul. 28-30, 1994, Turku, Finland.

Wilson, J. et al., "Toxicology and biocompatibility of bioglasses," *J. Biomedical Materials Res.*, 1981, pp. 805-817, vol. 15.

Wozney, J., "Bone morphogenetic proteins," *Progress in Growth Factor Research*, 1989, pp. 267-280, vol. 1.

Wozney, J. et al., "Growth factors influencing bone development," *J. Cell Sci. Suppl.*, 1990, pp. 149-156, vol. 13.

Yannas, I., "Viscoelastic Behavior and Certain Transitions of Gelatin-Nonaqueous Diluent Systems," *Princeton Univeristy Thesis*, 1966.

Yazdi, M. et al., "Postmortem degradation of demineralized bone matrix osteoinductive potential," *Clinical Orthopaedics Rel. Res.*, Jan. 1991, pp. 281-285, vol. 262.

Younger, E. et al., "Morbidity at bone graft donor sites," *J. Orthopaedic Trauma*, 1989, pp. 192-195, vol. 3, No. 3.

Zimmer, Inc., "Bone Grafting," *Teaching Materials on Bone Grafting for use by Zimmer, Inc's Collagraft® sales representatives*, 1993.

Zimmer, Inc., "Collagrafte Bone Graft Matrix (Nonosteoinductive Bone Void Filler)," *Collagraft® Bone Graft Matrix (Nonosteoinductive Bone Void Filler product information)*, May 1993.

Zimmer, Inc., "Collagraft® Strip Bone Graft Matrix," *Collagraft® Strip Product Information*, 1994.

Zimmer, Inc., "Fracture Management: Collagraft® Bone Graft Matrix (Nonosteoinductive bone void-filler): The new standard for bone grafting," *Collagraft® product information*, 1993.

Zimmer, Inc., "Highlights of safety and effectiveness studies for Collagraft® Bone Graft Matrix (Nonosteoinductive Bone Void Filler)," *Collagraft® product information*, 1992.

\* cited by examiner

TB-101

Selected Bone Grafting Materials

| Graft Material | Category | Physical Form | Distributor | Notes |
|---|---|---|---|---|
| Collagraft | conductive | Paste of Collagen TCP and HA | Zimmer | Inappropriate for large grafts. HA not resorbable. Expensive. |
| Norian | conductive | Reactive Paste which solidifies | SRS | New, interesting results, so far. Inappropriate for large grafts |
| Corraline HA | conductive | Calcined Coral 'Foam' of HA | Interpore | Good mechanical properties, difficult handling. |
| Powdered HA | conductive | Particulate HA, in a variety of presentations | Numerous | Problems with migration from implant site. Not resorbable. |
| Bioglass | conductive | $SiO_2$, $Na_2O$, $CaO$, $P_2O_5$ glass, forms HA-carbonate *in-vivo* | U.S. Biomaterials | Problems with migration from implant site. Not resorbable. |
| Autograft bone | inductive | Usually iliac or tibial crest wedge or just marrow | N/A | Up to >20% explant site morbidity. (Younger) |
| Allograft whole bone | conductive or inductive | Whole Bone Segments or chips, often including articular components. Either Frozen or Freeze-dried | University of Florida Tissue Bank, (UFTB), other tissue banks | Inductive if processing and sterilization is limited. Conductive if over-processed. Perceived problem with disease transmission. |
| Grafton | inductive | DBM in Glycerol matrix, provided pre-loaded in syringe | Osteotech | Problems with migration from implantation site.(Frenkel) 778 Glycerol is a neurolytic agent. |
| DBM | inductive | Powdered or Chips, provided Freeze-dried | UFTB, other tissue banks | Problems with migration from implantation site. (Lasa; Frenkel) |

| Bone Demineralization Procedure | | |
|---|---|---|
| Step No. | Procedure | Purpose |
| 1 | harvest long bones aseptically, remove adherent tissue | |
| 2 | grind bones at 4°C to 80 microns minimum size | powder demineralizes more rapidly |
| 3 | soak at 4°C in hydrogen peroxide (3%), 24 hours | oxidizes proteins, reduces antigenicity, antiseptic |
| 4 | soak at 4°C in 70% ethanol, 24 hours | defatting of bone, reduces antigenicity, antiseptic |
| 5 | soak at 4°C in 0.5N HCl, 24 hours | dissolves and removes mineral components, removes acid soluble proteins, reduces antigenicity, antiseptic |
| 6 | sieve to separate particles in ranges 80-400 µm, >400 µm, and <80 µm, discard 80µm | 80-400µm fraction is sold as DBM powder, >400 µm is sold as chips, <80 µm is engulfed by macrophagic activity *in vivo* and is ineffective, so it is discarded |
| 7 | lyophilize | allows storage at room temperature for up to 4 years, reduces antigenicity |

Figure 2.

Figure 3. Kinematic Viscosity (centistokes) versus Concentration (%) of Human Gelatin Processed at Various Temperatures in Phosphate Buffered Saline Solution
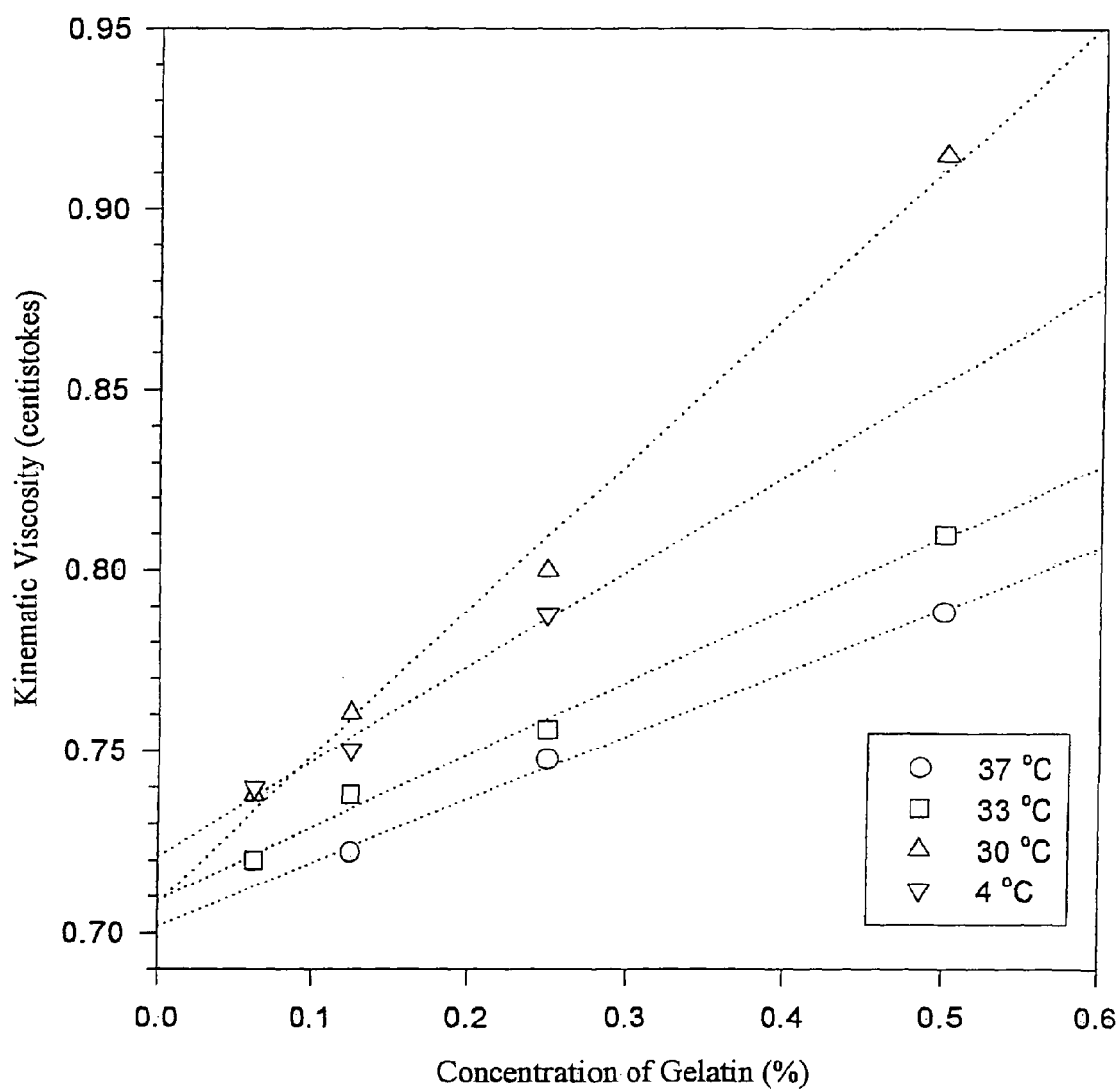

BONE PASTE

CROSS REFERENCE TO RELATED APPLICATION

This application is a continuation of U.S. application Ser. No. 08/816,079, filed Mar. 13, 1997.

BACKGROUND OF THE INVENTION

1. Field of the Invention

This invention relates to a new osteogenic, osteoinductive composition for use in the field of orthopedic medicine to achieve bone fusions, fusion of implants to bone, filling of bone defects, or any other application in which an osteoinductive, osteogenic composition is desirable.

2. Background

More than 100,000 bone grafting procedures are performed every year in the United States alone. (Cornell). In the majority of reconstruction procedures, the graft material is used as a filler between bone particles in the belief that continuous contact between particles of bone leads to more rapid and complete healing at the repair site (as well as greater mechanical integrity). (Bloebaum). In the cases of bone augmentation and spinal fusion, these bone grafts may make up the entire structure of the graft, since there are no bone fragments in the area. With the possible exception of one product (whose use guidelines do not allow this), all bone grafting materials require surgical placement with the requisite incisions.

Osteogenic bone grafting materials may be separated into two classes, namely those which are osteoconductive, and those which are osteoinductive. While the exact definition of these terms remains a matter of debate, it can be said that osteoconductive implants "conduct" bone growth across defects when implanted into osseous tissue. (Einhorn). Osteoinductive implants, on the other hand, have the ability to "induce" cells in the area to generate bone of their own accord. (Einhorn). These osteoinductive implants will cause the generation of bone even when they are implanted into non-osseous tissue (e.g. subcutaneous or intramuscular implantation). (Einhorn; Benedict; Strates; Urist).

All of the artificially produced bone-grafting materials available today fall in the osteoconductive category of grafts. Among these are BIOGLASS® ($SiO_2$, $Na_2O$, $CaO$, $P_2O_5$ glass), NORIAN® (calcium phosphate bone cement; available from Synthes), COLLAGRAFT® (collagen-containing bone graft material; available from Zimmer), corraline hydroxyapatite, powdered hydroxyapatite, crystalline and amorphous hydroxyapatite (hydroxyl apatite), and a number of other products. All of these implants rely on their similarity to natural bone hydroxyapatite. A likely mechanism for bone conduction lies in the ability of these materials to enhance diffusion of trophic factors and cells over their very large surface areas and the mechanical support which they provide to growing tissues. FIG. 1 provides a list of relevant properties of selected bone graft materials.

The other category of bone grafting materials currently available is encompassed by autograft or allograft bone. If not too harshly processed, these materials are generally osteoinductive.(Yazdi). Since they are tissue transplants, their use imposes certain risks. Autografts have been associated with harvest site morbidity in excess of 20%. (Younger). Frozen or freeze-dried allografts induce some immune response, and if not properly screened, can be associated with disease transmission. (Hordin). The last variety of allografts is demineralized bone matrix.

Demineralized Bone Matrix (DBM) was first described by Senn in 1889. (Senn). It was rediscovered, largely by accident, and thoroughly studied by Urist and Strates in the late 1960's. (Strates; Urist). It has since become a major product of tissue banks around the world. As the name implies, it is bone which has been demineralized by treatment with acid. A detailed outline of the process for producing this product is provided in FIG. 2.

DBM has the ability to induce the formation of bone even in non-osseous tissues within 4 weeks. (Strates; Urist; Lasa). The standard technique for determining the activity of DBM is to implant it subcutaneously or intramuscularly. (Nathan). It is believed that the major active factor in DBM is one or more bone morphogenetic proteins (BMP), (see U.S. Pat. No. 4,294,753, herein incorporated by reference). Other growth factors, including but not limited to TGF-beta, (see U.S. Pat. No. 5,422,340, herein incorporated by reference), platelet derived growth factor (PDGF), and the like, may be important for this function also.

BIOGLASS® is a bone grafting material, which is a $SiO_2$, $Na_2O$, $CaO$, $P_2O_5$ glass, which has the ability to produce a bio-active surface layer of hydroxylapatite carbonate within minutes of implantation. (Hench).

Two problems are associated with the use of DBM or BIOGLASS®. Both of these materials are supplied as large particles, and do not always stay in the area into which they are implanted. (Scarborough; Frenkel). Also, due to their coarse nature, they are hard to mold and handle in the operating room. Accordingly, there is the need for a product which does not allow for particle migration, while also being easier to use in the operating environment.

As noted in table 1, in recent years, several bone-filling surgical pastes have become commercially available. These products range from simple mixtures of saline with a sand-like powder to a recently released gel, known as GRAFTON®, a glycerol-based, non-cross-linkable composition (Osteotech, Inc.). All of these products are used in orthopedics to repair bone defects, such as voids, cavities, cracks etc. Such defects may be the result of trauma or may be congenital, and the known pastes may be used to patch or fill such defects, or build upon existing bony structures. The ultimate goal of such treatments is that the paste will induce bone formation to replace the paste while retaining the form created by the surgeon when applying the paste.

Desirably, a bone paste would be osteoconductive (i.e. it conducts bone cells into a region) and osteoinductive (i.e. stem cells are induced to differentiate into bone forming cells which begin production of new bone). In general, bone pastes known in the art are osteoconductive, with only weak osteoinductive effects. Accordingly, such known pastes are inadequate for filing of large voids and frequently do not effect proper bone formation even in small voids. All currently available bone pastes, including those that exhibit some osteoinductive activity, are difficult to handle, do not adequately remain at the site of implantation, or both.

Thus, one commercially available product, GRAFTON®, (see U.S. Pat. No. 5,484,601) is a non-cross-linkable composition of demineralized bone powder suspended in a polyhydroxy compound (e.g. glycerol) or esters thereof, optionally including various other ingredients, including gelatin. It is considered likely that this material is rapidly washed away from the implant location as the carrier matrix is glycerol, which is water soluble.

U.S. Pat. Nos. 5,236,456 and 5,405,390 (O'Leary and Prewett) outline an "osteogenic" gel composition which is made from demineralized bone matrix (DBM) by treating with concentrated acid (3 M HCl) and heating to between 40 and 50° C. The patent briefly describes mixing the gel with DBM and several other components. However, the method of manufacturing the gel composition is such that it produces mostly collagen fibers (i.e. the temperature elevation is insufficient to produce gelatin). As a result, the collagen fibers are not soluble in neutral solutions. To obtain a gel, the patent specifies that the collagen must be dissolved in acid of low pH (e.g. HCl or 1% acetic acid, at a pH of less than 4.0). However, compositions of low pH are not typically very compatible with biological implantations. It is also noted that at column 5, line 20, and column 6, line 15, it is specified that the temperature at which the gel solidifies is 0-5° C., which precludes gellation in vivo.

U.S. Pat. No. 4,440,750 (Glowacki and Pharris) outlines a standard enzymatic technique for extracting collagen from tissue using Pepsin. A highly refined collagen is obtained from animal sources, which is then reconstituted prior to forming the working composition. The collagen will not readily cross-link without the addition of other chemicals (e.g. aldehydes, chondroitin sulfate), which they do not specify in the composition. There is no mention of a set temperature or any reference to cross-linking behavior.

In U.S. Pat. Nos. 4,394,370 and 4,472,840, (Jefferies), complexes of reconstituted collagen with demineralized bone or solubilized bone morphogenetic protein, optionally cross-linked with glutaraldehyde, were reported to be osteogenic when implanted in vivo. The reconstituted collagen of these patents is pulverized, lyophilized, microcrystalline collagen which has been dialyzed to remove the hydrochloric acid used in collagen preparation. Accordingly, the composition of those patents does not involve the conversion of collagen to gelatin prior to formation of the composition. Hence, the composition would not exhibit the thermal cross-linking behaviour of the instant composition.

In U.S. Pat. No. 4,678,470 (Nashef et al.) disclosed a non-resorbable bone-grafting material comprising demineralized bone matrix that had been cross-linked by treatment with glutaraldehyde, or like cross-linking agent, suspended in a gelatinous or semi-solid carrier. Given that the demineralized bone of that patent is chemically cross-linked, its bone inductive properties are considered to be destroyed and the composition essentially forms a structural filler or matrix into which recipient bone may grow.

In WO 89/04646 (Jefferies), a bone repair material having good structural strength was disclosed. The material comprised a demineralized bone matrix which had been surface activated by treatment with glutaraldehyde or like cross-linking agent to increase the binding thereof to biocompatible matrices. The resulting material has such a rigid structure that, prior to implantation into a biological recipient, the material may be machined.

The bone paste of the present invention meets the needs in the art by providing a material that is easy to handle and store, which adheres to the site of implantation, displays both osteoconductive and osteoinductive activities, is thermally cross-linkable, and is substantially bioabsorbable. Preferably, the composition is provided as a gel which contains mineral and protein components which have been clinically shown to induce rapid bone ingrowth. The composition may be delivered to the surgeon in a pre-loaded syringe, ready for use. Preferably, at a first temperature, the gel is easily formable into any shape, and is adhesive. Once inside the biological milieu, or at a second lower temperature, the gel desirably hardens as a rubbery solid, which does not wash away or migrate from the site of implantation. Upon ingrowth of bone, the implant material becomes completely incorporated into the biological system. The mode of making and using this composition is set forth in detail below.

BRIEF SUMMARY OF THE INVENTION

A bone paste useful in the orthopaedic arts, for example in the repair of non-union fractures, periodontal ridge augmentation, craniofacial surgery, implant fixation, arthrodesis of spinal or other joints, including spinal fusion procedures, or any other procedure in which generation of new bone is deemed necessary, is provided by a composition comprising gelatin and additional osteogenic components. The gelatin is preferably thermally cross-linkable, and the osteogenic components are selected from:
(i) demineralized bone, preferably derived from the species into which the bone paste is to be implanted; or
(ii) bioactive glass ceramic, BIOGLASS®, bioactive ceramic, calcium phosphate ceramic, hydroxyapatite, hydroxyapatite carbonate, corraline hydroxyapatite, calcined bone, tricalcium phosphate, like material, or mixtures thereof; or
(iii) bone morphogenetic protein, TGF-beta, PDGF, or mixtures thereof, natural or recombinant; or
(iv) mixtures of (i)-(iii).

Where present (ii) or like material is included to enhance the range of manipulable characteristics of strength and osteoinduction exhibited by the composition. Where present, (iii) reduces the need for demineralized bone, which otherwise provides a source of osteoinductive factors.

Demineralized bone has been shown to be highly effective in inducing bone formation. The gelatin provides a cross-linkable, adhesive and easily manipulated matrix in which the osteoconductive and osteoinductive elements of the composition are carried. Other factors, such as antibiotics, bone morphogenetic or other proteins, whether derived from natural or recombinant sources, wetting agents, glycerol, dextran, carboxymethyl cellulose (CMC), growth factors, steroids, non-steroidal anti-inflammatory compounds, or combinations thereof or any other material found to add to the desirable properties of the essential composition of this invention may be included.

The composition may be freeze-dried or pre-constituted, and may be provided in a convenient dispensing device, such as a pre-loaded syringe. The gel is preferably in a liquid or highly malleable state at temperatures above about 40° C., but sets up as a hard gel at or preferably slightly above the body temperature of the organism into which it is implanted (e.g. at 38° C. in humans).

BRIEF SUMMARY OF THE FIGURES

FIG. 1 is a chart of existing bone grafting materials.

FIG. 2 represents a bone demineralization process.

FIG. 3 is a graph of the kinematic viscosity (centistokes) versus concentration (%) for human gelatin processed at various temperatures in phosphate buffered saline solution (PBS).

DETAILED DESCRIPTION OF THE INVENTION

Figure 4A:
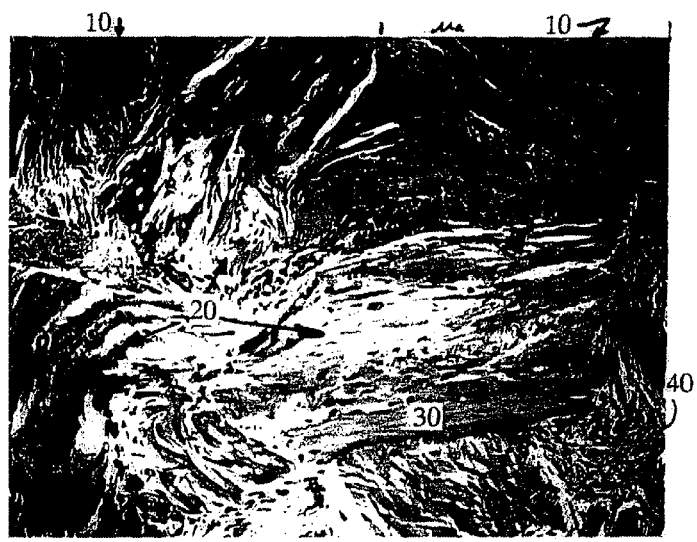
FIG. 4A is a photomicrograph of a section of an implant comprising demineralized bone matrix (DBM) without any carrier after four weeks intramuscularly in a rat.

It will be appreciated by those skilled in the art that the specifics of the composition of this invention, its method of preparation and use are applicable to such compositions for use in any vertebrate species. Nonetheless, because human use is considered likely to be the principal orthopedic application of this new material, the following description concentrates on exemplifying this material for human applications.

The composition of this invention comprises gelatin and additional osteogenic components. The gelatin is preferably thermally cross-linkable, and the osteogenic components are selected from:
(i) demineralized bone, preferably derived from the species into which the bone paste is to be implanted; or
(ii) bioactive glass ceramic, BIOGLASS®, bioactive ceramic, calcium phosphate ceramic, hydroxyapatite, hydroxyapatite carbonate, corraline hydroxyapatite, calcined bone, tricalcium phosphate, like material, or mixtures thereof; or
(iii) bone morphogenetic protein, TGF-beta, PDGF, or mixtures thereof, natural or recombinant; or
(iv) mixtures of (i)-(iii).

The composition is fluid at a first temperature (e.g., above 38° C.) and becomes thermally cross-linked at or just above a second temperature, corresponding to the normal body temperature of the organism into which the composition is to be implanted (e.g., at 38° C. in humans).

The terms "thermally cross-linked" or "thermally cross-linkable" are used herein to describe the property of a composition which contains molecules which, at or below a given temperature and concentration, associate in such a fashion as to result in gelation of a solution containing these molecules.

The term "substantially bioabsorbable" is used herein to describe the property of a material able to cooperate in and become incorporated with new bone formation. Accordingly, for example, demineralized bone matrix which has been chemically cross-linked with an agent such as glutaraldehyde, is not considered to be substantially bioabsorbable. However, demineralized bone matrix itself, bioactive glass or like ceramics, gelatin, and bone morphogenetic factors are all considered to be substantially bioabsorbable as they cooperate in new bone formation, rather than purely providing structural rigidity or support.

The gelatin acts as a carrier phase and has the ability to thermally cross-link over a very small temperature range. This thermal cross-linking reaction is largely controlled by physical entanglement and hydrogen bonding between chains, and so is dependant on concentration and temperature. (Sperling). Additionally, since gelatin has been used extensively in the medical market, its in vivo properties are thoroughly studied. (McDonald). The gel-foam sponge is the most familiar application of this biopolymer. Studies have indicated that gelatin is only mildly antigenic upon implantation, and is comparable in some of its properties to collagen, (McDonald). However, collagen does not exhibit the thermal cross-linking property so important to the composition of this invention.

Where present, the bioactive glass, such as BIOGLASS®, bioactive ceramic, calcium phosphate ceramic, hydroxyapatite, hydroxyapatite carbonate, calcined bone, tricalcium phosphate, or like material, is included to enhance the range of manipulable characteristics of strength and osteogenesis (osteoinduction and osteoconduction) exhibited by the composition.

The manufacture of gelatin is based on the partial hydrolysis of collagen. Collagen is available from skin, bone, cartilage, tendon and other connective tissue. Skin and bone yield Type I and Type III collagen molecules, while tendon yields nearly pure Type I collagen, and cartilage yields a mixture of Type II and rarer types of collagen molecules. Gelatin molecules resemble collagen triple helices, however, they are partially hydrolyzed. As a result, in solution they have little organization. But, as the solution cools, the gelatin molecules begin to form helical structures. As the solution cools further, the viscosity increases and a phase transformation from a solution to a gel occurs. This phase change is reversible when heat is added.

The set time and set temperature of a gelatin solution are dependent on the concentration of gelatin in solution, the molecular weight, or intrinsic viscosity, of the gelatin molecules, and the pH of the solution. At the isoelectric point, or the pH at which the gelatin molecules are electrically neutral, the set time is the shortest.

Collagen can be partially hydrolyzed by several methods. The Type A process is the simplest and most rapid process, in which dilute acid (e.g. less than 1 M HCl) is used to partially hydrolyze the collagen. Type A processing is generally used with porcine skin and demineralized bovine bone. The Type B process uses an alkaline solution to partially hydrolyze the collagen. Type B processing is generally used with bovine hide and demineralized bovine bone. Finally, enzymes, such as pepsin, may be used to partially hydrolyze collagen. Pepsin preferentially cleaves peptide bonds between aromatic amino acids. Pepsin also acts as an esterase, but amides of amino acids are not hydrolyzed.

As one example of this method, the gelatin is prepared from the bones of the species into which the compositions are to be implanted, by crushing and defatting the bones followed by soaking for about 24 hours in approximately 300 mg/L pepsin in a 0.5 M acetic acid at 33° C. The pH of the resulting solution is brought to 9.0 with sodium hydroxide to denature the pepsin, then it is returned to 7.0 with hydrochloric acid. The temperature of the solution is raised to 60° C. for about 15 to 30 minutes and returned to 4° C. to effect denaturation of remaining collagen and complete conversion to gelatin. The resulting solution is filtered to remove particulates and dialyzed against distilled water for 48 hours in a 50K-100K molecular weight cut-off (50K-100K MWCO) dialysis membrane. After lyophilization, the gelatin is redissolved in phosphate buffered saline (PBS) or water to an effective concentration of about 30-45 weight percent of gelatin in solution.

The gelatin content of the composition is desirably between about 20-45% (w/w). The gelatin may be derived from the same or different species than that into which the composition is to be implanted. For example, human, porcine, bovine, equine, or canine gelatin is derived from collagen sources such as bone, skin, tendons, or cartilage, and may then be mixed with DBM or other osteogenic materials. As noted above, the collagen is converted to gelatin via, liming, acidification or by enzymatic extraction, for example by pepsin or like enzymatic treatment, followed by denaturation by heat or other means. The gelatin may be derived from tissue by mastication of the tissue, followed by an extended treatment capable of breaking cross-links in the long collagen chains. In one embodiment, the tissue is ground then soaked for about 24-72 hours at between about 2-40° C. in dilute acid, such as 0.1 normal acetic acid. Preferably, an enzyme such as pepsin at a sufficiently high concentration is added. Pepsin concentrations of between about 10-20,000 i.u./liter, 100-2,000 i.u/liter, or like concentrations are added to the dilute acid at the start of the treatment, with the period of treatment being adjusted according to the enzyme concentration used. Solids are removed from the composition, for example by centrifugation, and the supernatant material in solution having a molecular weight of about 50,000 daltons or higher is retained. This may be achieved by any of a number of methods known in the art including, but not limited to, dialyzing the supernatant in a 50,000 dalton molecular weight cut-off membrane against several changes of solution, ultrafiltration against a membrane having a like molecular weight cut-off, (MWCO) or gel permeation chromatography through a medium having a 50,000 dalton molecular mass cut-off. It will be recognized by those skilled in the art that the higher the MWCO of the gelatin, the lower the yield. Accordingly, lower MWCO gelatin preparations, down to abut 1000 dalton MWCO's could be used, recognizing that undesirable low molecular weight species might thereby be retained.

The gelatin solution resulting from the foregoing extraction is preferably denatured, for example by heat-treatment to above about 50° C. The denatured protein is then stored in a frozen state or it may be freeze-dried or precipitated, for example in a volatile organic solvent, and reconstituted in a solution, such as an isotonic saline solution, at a concentration of between about 30-45% (w/w) gelatin.

The demineralized bone is preferably in a powdered form, and is preferably composed of particles in the size range between about 80-850 µm in diameter. Methods for producing demineralized bone powder are known in the art (see for example U.S. Pat. No. 5,405,390, herein incorporated by reference for this purpose), and are not, therefore, elaborated here. Demineralized bone powder, extracted by standard techniques, is mixed with the gelatin solution prepared as described above, to form a composition comprising about 0-40% (w/w) demineralized bone powder. Where present, bone morphogenetic proteins (BMP) reduce the percentage of DBM required in the composition. The BMP is preferably present at a concentration of between about 0.0001 to 0.1 mg/ml, 0.001 mg/ml to 0.01 mg/ml, or like concentration, depending on the amount of DBM present (0-40% w/w).

In certain embodiments of this invention, and for particular orthopaedic applications in which strength of the bond formed by the bone paste is important, addition of a bioactive glass is preferred. When added, the bioactive glass lowers the adhesiveness of the composition, but increases the stiffness of the composition upon setting. Accordingly, a bioactive glass, such as BIOGLASS® having a diameter of between about 0.5-710 µm, is added to the gel/demineralized bone composition. In addition, a composition comprising between about 0-40% (w/w) of bioactive glass with the gelatin forming 20-45% (w/w) of the composition is also contemplated.

Compositions prepared as described above are easily extruded from a syringe, particularly when the temperature is elevated to above about 40° C., for example by immersion in a water bath, by limited treatment in a microwave, by placement in a syringe warmer, or any of a number of other methods for heating the container. The extruded gel is resilient, sticky and easily formable into any desired shape. In addition, the composition retains its strength and is poorly soluble in saline once it sets-up.

Accordingly, having generally described the composition of this invention, and taking into account the specifics of the exemplary support provided below, the following guidelines for the preparation and use of the composition of this invention are provided:

The gelatin from DBM should be prepared at a temperature between about 30 and 37° C. While the yield is higher (60%) at 37° C., the quality, based on measured kinematic viscosity, is slightly lower than that produced at 30° C. Preferably, the gelatin is produced by limited hydrolysis of collagen with the assistance of an enzyme, such as pepsin, or like enzyme. A concentration of pepsin set at 300 U/L-500 U/L works well, but those skilled in the art will recognize that a wide range of enzyme concentrations could be tested, based on what is disclosed herein. Those skilled in the art will recognize that acid or alkaline processing of skin and tendon may be an alternative to the pepsin technique.

The final composition preferably comprises gelatin having a viscosity of about 3600 centipoise at 44° C. (when measured in the linear range of a viscosity/sheer rate plot-0.87/s), or a kinematic viscosity of about 0.7 centistokes at 44° C. The concentration of the gelatin in the carrier phase (i.e. absent added osteogenic components) is preferably about 30-45% (w/w), (approximately 50-60% w/v), to ensure that gelation at 38° C. will occur in a reasonable amount of time. Naturally, those skilled in the art will recognize that, depending on the species of the organism into which the composition is to be implanted, different temperatures may be required. These needs are accommodated by altering the gelatin concentration, increasing the concentration if a higher gel temperature is desired, and lowering the concentration if a lower gel temperature is desired.

The DBM content of the composition is defined herein by the concentration required to obtain bone formation similar to that seen with DBM alone. We have found that about 5-40% (w/w) DBM in the composition is effective. Anything lower than about 5% seems to do very little by way of bone formation, unless added BMPs (component iii) are present in the composition, in which case the DBM concentration may be substantially reduced or eliminated altogether. Naturally, based on this disclosure, those skilled in the art will recognize that by addition of different concentrations and compositions of bone morphogenetic proteins or other osteogenic or osteoinductive factors, the weight percent of DBM in the composition may be manipulated up or down. In addition, it will be recognized that, depending on the species into which the composition is implanted, the DBM weight percent may need to be adjusted up or down.

We have found in in vivo studies that the compositions with DBM contents from 15 to 33% all produce calcified tissue. We have found that there is a good correlation between the amount of DBM in the composition and the level of bone induction, as long as the DBM concentration is greater than about 19% (w/w). About 38-40% (w/w) is the upper mass limit for DBM. Accordingly, 0-40% (w/w) DBM, and more preferably 5-30% (w/w), 7-33% (w/w) or 15-25% (w/w) is desirable for this component.

We have observed histologically that, subsequent to implantation into an animal, the gelatin phase is totally absorbed within about 2 weeks. Additionally, cartilage and mineralized bone formed within two weeks, with mature bone being evident by about the fourth week. The animals in these studies did not exhibit any gross health problems or any indications of irritation, hematoma, soreness, fever, or weight loss during the study. The composition according to this invention, whether it comprises gelatin and osteogenic components (i-iv) may act as a carrier for cortical, cancellous or cortical and cancellous bone chips. Such compositions are useful for filling larger bone voids. In addition, when these bone chips are not demineralized, they provide an added spectrum of biological properties not exhibited by the gelatin alone or the gelatin plus osteogenic components (i-iv). When present, it is preferred for such bone chips to be in the size range of about 80 µm to about 10 mm.

In a further embodiment of this invention, the composition of gelatin and osteogenic components (i-iv) is injection molded, vacuum molded, rotation molded, blow molded, extruded or otherwise formed into a solid form. Such forms would desirably take the form of vertebral disks, acetabular hemispheres, tubes, ellipsoid shapes for void filling, and intramedullary plugs, which are useful to plug the intramedullary canal of various bones (i.e. the marrow containing portion of the bone) to prevent bone cement from entering healthy bone tissue. These forms are produced, for example, by raising the temperature of the composition above its liquefaction temperature (e.g. about 45° C.), and allowing the composition to gel in a mold of appropriate shape. For such forms, the gelatin content is preferably made as high as possible to ensure that the form remains solid upon grafting into a vertebrate recipient.

Those skilled in the art will recognize the many orthopedic applications of the bone paste of this invention. However, by way of illustration rather than limitation, for purposes of arthrodesis of the spine, one particularly preferred mode of using this composition would be at an early stage of vertebral disk degeneration or subsequent to trauma. Diagnosis of trauma or degeneration is followed by formation of a small orifice, or a plurality of small orifices in the intervertebral cartilage at the site of degeneration. The bone paste is then injected into the intervertebral space to induce arthrodesis. A similar procedure could be used with other joints or bone damage.

Having generally described the invention, the following examples are provided to show specific features and applications of the invention. It should be recognized that this invention is in no way limited to the specifics of the examples as set forth below, and that the limits of this invention are defined by the claims which are appended hereto.

EXAMPLE 1

Gelatin Production Kinematic Viscosity and Critical Concentration for Gelation at 38° C.

In this experiment, the source of collagen was from demineralized human cortical bone powder in the size range of 250-850 μm. The demineralized bone matrix powder (DBM), 0.5 M. acetic acid solution, and pepsin were added to a centrifuge tube. The centrifuge tube was tumbled for 24 hours at the desired temperature: 4° C., 30° C., 33° C. or 37° C. The pH was adjusted to 9.0 then down to 7.0 with 1 N NaOH and 1N HCl, respectively, deactivating the pepsin. The solution was placed in a 60° C. water bath for 15 minutes, then quenched in ice water. The solution was centrifuged and the supernatant was poured into dialysis membrane tubing with a 1000 Daltons molecular weight cut off. The supernatant was dialyzed to obtain a 1000:1 dilution factor, frozen and lyophilized until completely dry. This experiment was performed in quintuplicates for each temperature.

The kinematic viscosities of dilute concentrations of gelatin, 0.0625 w/v %, 0.125 w/v %, 0.25 w/v %, and 0.5 w/v % in phosphate buffered saline solutions (pH 7.4 at 25° C.), were measured with an Ubbelhode viscometer at 44° C. The kinematic viscosities of human gelatin processed at 4° C., 30° C., 33° C., and 37° C., were measured in duplicates, except for 33° C. which was only measured once. The kinematic viscosities (centistokes) were graphed versus concentration of human gelatin solution, FIG. 3. The linear regression was extrapolated to zero to determine the kinematic viscosity at zero concentration. The optimum processing temperature was determined by the temperature that yielded the highest solution viscosity at zero concentration, largest slope of the linear regression, greatest yield, and lastly, the gelatin that produced a solid bone composite at slightly above human body temperature.

As the processing temperature increased, the yield of gelatin, normalized for the same pepsin to DBM ratio (0.03% (w/v) pepsin/1 g DBM), increased. The kinematic viscosity at zero concentration, or y-intercept, followed a reverse trend. As the processing temperatures increased, the extrapolated kinematic viscosities decreased, Table 1.

The human gelatin processed at 30° C. had the highest slope on the kinematic viscosity versus concentration plot, 0.40 (centistokes/%), followed by the human gelatin processed at 4° C., 0.26 (centistokes/%), the human gelatin processed at 33° C., 0.21 (centistokes/%), and lastly the human gelatin processed at 37° C., 0.17 (centistokes/%), Table 1.

In order to correlate the kinematic viscosities to molecular weight of gelatin, the kinematic viscosities must be translated into intrinsic viscosities. However, the intrinsic viscosities were undefined due to the polyelectrolytic nature of gelatin. As a result, a direct relationship between viscosity and molecular weight of human gelatin can not be made.

TABLE 1

Physical properties of human gelatin and human gelatin in phosphate buffered saline solution. Human gelatin was processed at 4° C., 30° C., 33° C., and 37° C., resulting from 1 g of DBM and 0.03 w/v % pepsin solution in 0.5 N acetic acid:

| Human Gelatin Processed at Various Temp. | Average Yield Percent by Weight | Extrapolated y-intercept (centistokes) | Slope of Linear Regression (centistokes/%) | $r^2$ Value of Linear Regression |
|---|---|---|---|---|
| 4° C. | 6% (n = 5) | 0.72 (trial 1&2) | 0.26 (trial 1&2) | 0.985 (trial 1&2) |
| 30° C. | 18% (n = 5) | 0.71 (trial 1&2) | 0.40 (trial 1&2) | 0.993 (trial 1&2) |
| 33° C. | 30% (n = 4) | 0.71 (trial 1) | 0.21 (trial 1) | 0.994 (trial 1) |
| 37° C. | 60% (n = 5) | 0.70 (trial 1&2) | 0.17 (trial 1&2) | 0.996 (trial 1&2) |

The set temperatures for various bone paste compositions were determined, Table 2. Human gelatin made from DBM via pepsin at 33° C., 35° C., and 37° C. was used in the bone paste compositions. Gelatin concentrations were varied from 19 w/w % of total composite to 25 w/w % of total composite (corresponding to 40 w/v % to 60 w/v % gelatin in the carrier matrix) in a pH 7.4 phosphate buffered saline solution (PBS). All bone paste composites tested contained DBM at a concentration of 33 w/w % of the total composite. Different ambient temperatures were used to test whether the bone paste was solid or liquid, 45° C., 43° C., 41° C., 40° C., 38° C., and 35.5° C. The set temperature was determined both by subsequent lowering of the ambient temperature and raising of the ambient temperature.

TABLE 2

Ambient temperatures corresponding to solidified (non-syringe-able) bone paste composites.

| Human Gelatin as a Percent of Total Composite Weight | 37° C. Process Temp | 35° C. Process Temp | 33° C. Process Temp |
|---|---|---|---|
| 25 w/w % | <35.5° C. | <35.5° C. | 40° C. |
| 24 w/w % | <35.5° C. | <35.5° C. | <35.5° C. |
| 22 w/w % | <35.5° C. | <35.5° C. | <35.5° C. |
| 21 w/w % | <35.5° C. | <35.5° C. | <35.5° C. |
| 19 w/w % | <35.5° C. | <35.5° C. | <35.5° C. |

Accordingly, the critical concentration of gelatin in a bone paste composite that was solid at slightly above human body temperature, 38° C. to 39° C., was 25 w/w % of the total composite for human gelatin, processed at 33° C., and with 33 w/w % of the composite being DBM, the remainder being PBS. The human gelatin processed at 33° C. had a zero concentration kinematic viscosity of 0.71 centistokes. Human gelatin solutions of lower kinematic viscosities were found to have critical concentrations in excess of about 25 w/w %. Correspondingly, gelatins with viscosities higher than about 0.71 centistokes are expected to thermally cross-link at concentrations lower than about 25% (w/w).

EXAMPLE 2

In Vivo Bone Paste Composition and Activity

This study demonstrates that the bone paste of this invention is osteoinductive. In addition, this study demonstrates particle sizes for the DBM component of the composition which operate well in promoting new bone growth in an animal into which it is implanted.

The intramuscular rat model is the standard model for testing the osteoinductivity of demineralized bone and other osteoinductive factors. Strates et al. have used this model for many years (Strates).

As noted in Example 1 above, we determined that for gelation at 38° C., a gelatin solution concentration of 40-60% w/v (30-45% w/w of the solution absent added osteogenic components) is required. At this concentration, gelatin acting as a carrier matrix thermally cross-links at 38° C. within approximately 8 minutes. In this study we addressed the question of how much DBM must be present in this fixed 40-60% gelatin carrier matrix to induce bone formation which favorably compares with positive controls. We compared 4 different compositions of a DBM/Gelatin composite with both positive and negative controls in a rat intramuscular model.

A. Implant Preparation:

The femurs, tibiae, and fibulae were harvested from fresh-killed (within 24 hours, refrigerated at 4° C.) Sprague-Dawley rats. The diaphyses were cut from the bones and the marrow removed from the mid-shaft with a dissecting probe and sterile water wash. Mid-shaft segments were then demineralized in 0.6 M. HCl for 24 hours at 4° C. with the mass ratio of bone to acid maintained at 1/10 or lower. The bone segments were lyophilized and then mixed with dry ice and ground in a lab-scale bone mill. DBM powder was sieved and the fraction from 125-450 μm was retained.

A carrier matrix of 50% (w/v) gelatin was made by heating phosphate buffered saline (PBS) to 60° C. and then adding powdered porcine gelatin (Sigma, 300 bloom) and stirring vigorously. Carrier matrix was allowed to age for 15 minutes (to even out the distribution of gelatin in solution) and then it was allowed to cool to 50° C. DBM was added to the gelatin solution at this point in the following amounts: 0 (negative control), 15, 19, 24, and 33% w/w of the total composite. The composite was blended thoroughly by hand mixing.

Implants were prepared by ejecting a thread of composite onto a petri dish. These threads were cut into short segments (~4 mm.), weighed, and placed into sterile petri dishes. Positive controls were prepared by pelletizing DBM mixed with PBS in a centrifuge. To maintain pellet integrity during the hazards of surgery, these pellets were frozen and implanted as such.

B. Rat Surgery:

Young Sprague-Dawley rats (200-410 g) were anesthetized with 86 mg/kg Ketamine, and 13 mg/kg Xylazine administered intramuscularly (in the thigh). A parallel-midline incision was made from the tip of the sternum to just above the groin. The lateral aspects of the rectus abdominus were accessed by blunt dissection to either side of the animal. Three short incisions were made in the muscle on each side and the implants inserted, followed by 1 to 2 stitches with Prolenen¤ 3-0 suture (to mark the location and prevent the ejection of the implant mass). One positive or one negative control as well as two experimental compositions were inserted on each side. Implant locations were random except that each rat had one positive control on one side and one negative control on the contralateral side.

Animals were returned to their cages and provided food and water ad-lib. All members of the study group were kept for 4 weeks except one animal (R1) which was sacrificed after 2 weeks for histology.

After 4 weeks, animals were sacrificed with an overdose of Nembutal. The rectus abdominus was removed by sharp dissection, removing as much tissue as possible.

C. Explant Analysis:

Each muscle was notched to mark the superior side of the animal and placed into a labeled petri dish. The muscle was X-rayed with mammography equipment, using mammography film (DuPont). Roentgenograms were analyzed using a digital camera attached to an Apple LCII equipped with NIH Image 4.1 software. Images were thresholded to highlight the implant shadow and then the area of the shadow was determined by pixel counting.

Two of each variety of explant were removed from the muscle and fixed in 10% buffered formalin. Histological sections were taken and consecutive sections were stained with H&E and Masson's trichrome stain. These histological samples were examined by a qualified pathologist.

Remaining explants were cut from the muscle tissue and ashed in a muffle furnace for 4.5 hours at 700-750° C. Ash weight was determined and normalized to original implant weight. Ash was dissolved in 1.0N HCl and analyzed for calcium content by atomic absorption spectroscopy.

All analyses were conducted in a blinded manner with decoding done only after processing of the data was complete.

Figure 4B:
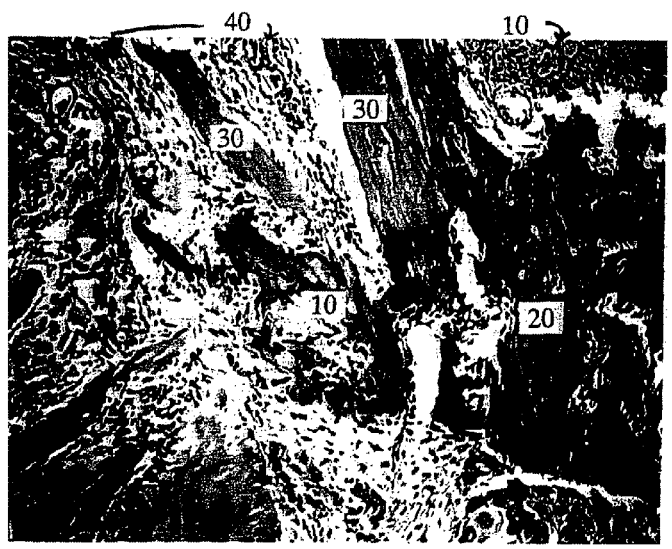
FIG. 4B is a photomicrograph of a section of an implant comprising 33% DBM in gelatin (i.e. the paste of this invention) after four weeks intramuscularly in a rat.

D. Histology:

Two week histology samples of 15% and 19% DBM composites indicated that bone formation was occurring, even at this early date. The route of bone formation is not readily apparent, but appears to be endochondral. Four week histology samples revealed that mature bone was formed at the site of implantation. The quality of bone formed was comparable to that of natural bone as shown by the ash and percent calcium analyses. All implants containing DBM were found to lead to the production of some bone. Those containing greater than about 20% DBM yielded the highest quality bone. FIGS. 4A and 4B provide photomicrographs of sections of implants after four weeks in vivo in the rat intramuscular model. We found that 33% (w/w) DBM in gelatin carrier (FIG. 4B) according to this invention produced as much new bone as pure, 100% DBM (FIG. 4A). In these figures, the following structures are evident: 10 is mature bone, as evidenced by red stain uptake from Masson's stain; 20 is new cartilage formation, as evidenced by uptake of blue stain from Masson's stain and the presence of cells; 30 is residual DBM, as evidenced by uptake of blue stain and the absence of cells, from which all cartilagenous and bone structures in the muscle cross section arose; and 40 is immature bone, as evidenced by light blue staining and the presence of cells. The cells seen are osteoclasts, degrading the newly formed cartilage, and osteoblasts, laying down new bone. In addition, vascular infiltration in the mature bone is evident in the Masson's stained sections, from which the black and white prints were made.

E. Compositional Analysis:

There was no statistically significant difference, using a $2\sigma$ test, in ash content between the negative control, the positive control, or compositions comprising 15% or 19% (w/w) DBM. This does not necessarily imply that these compositions do not work (examination of the Roentgenograms obviates this conclusion). Rather, it indicates that the sensitivity of the ash method does not allow the detection of the difference. Examination of the data for the 24% and 33% composites indicates that they are significantly better than 19%, 15%, and the negative controls, and are not significantly different from the (positive) control, see Table 3:

TABLE 3

| Composition (% DBM) | % Yield Ash/g Implant | Standard Deviation |
|---|---|---|
| 0 {−control} | 10.1 | 9 (n = 6) |
| 15 | 5.5 | 12.7 (n = 6) |
| 19 | 11.9 | 12.2 (n = 6) |
| 24 | 34.5 | 14.9 (n = 5) |
| 33 | 30.0 | 8.0 (n = 4) |
| 100 {+control} | 31.9 | 8.8 (n = 6) |

F. Atomic Absorption Spectroscopy:

The atomic absorption spectroscopy of ashed compositions of DBM/gelatin composites yielded the amount of calcium in the samples. The 15% and 19% compositions did not show a statistically significant difference from the negative controls. However, it is expected that with greater assay sensitivity, positive effects of DBM at concentrations as low as about 7% (w/w) in gelatin carrier would be measurable. The average calcium content produced by compositions greater than or equal to 24% appeared to be proportional to the amount of DBM, by weight, in the composition:

TABLE 4

Comparison between the atomic absorption spectroscopy results of ashed samples of six different DBM/gelatin composites explanted from rats after 4 weeks in vivo.

| Composition (% DBM w/w) | Average Ca Content/gram | Standard Deviation ($\sigma$) |
|---|---|---|
| 0 {(−) control} | 1.2 | 1.2 (n = 6) |
| 15 | 3.9 | 2.4 (n = 4) |
| 19 | 7.3 | 7.5 (n = 4) |
| 24 | 23.1 | 8.7 (n = 3) |

TABLE 4-continued

Comparison between the atomic absorption spectroscopy results of ashed samples of six different DBM/gelatin composites explanted from rats after 4 weeks in vivo.

| Composition (% DBM w/w) | Average Ca Content/gram | Standard Deviation ($\sigma$) |
|---|---|---|
| 33 | 28.0 | 4.4 (n = 4) |
| 100 {(+) control} | 81.3 | 30.0 (n = 5) |

G. X-Ray Digital Analysis:

Gross examination/comparison of the x-rays reveals that the 24% and 33% compositions are not significantly different from the (+) controls. The 15% and 19% compositions do not appear to generate significant bone. However, it is expected that with greater assay sensitivity, positive effects of DBM at concentrations as low as about 7% (w/w) in gelatin carrier would be measurable. No bone formation was apparent on the x-rays at the locations of the (−) controls. Accordingly, we conclude that DBM at a concentration of between about 24% to 33% (w/w) in gelatin is active in inducing bone formation. These same data indicate that concentrations of DBM below about 20% are less effective in generating significant bone in comparison to positive controls. It is noted that GRAFTON™ contains only 8% DBM in a glycerol carrier.

TABLE 5

| Composition (% DBM w/w) | Normalized Area (% of +ve control) | Standard Deviation ($\sigma$) |
|---|---|---|
| 0 {(−) control} | 0 | 0 (n = 10) |
| 15 | 2.8 | 1.9 (n = 7) |
| 19 | 4.1 | 4.2 (n = 7) |
| 24 | 33.0 | 15.2 (n = 10) |
| 33 | 36.7 | 14.9 (n = 10) |
| 100 {(+) control} | 100 | 43.1 (n = 10) |

EXAMPLE 3

Procedure for the Production Bone Paste of this Invention:

This example provides one procedure for the manufacture of bone paste from gelatin and demineralized bone. As fractions of the total mass of composition desired, the following components are weighed (percentages given are of total composite weight):

| | |
|---|---|
| Dry demineralized bone: | 0-40% (w/w) |
| Lyophilized thermally cross-linkable gelatin: | 20-45% (w/w) |
| BIOGLASS ®: | 0-40% (w/w) |
| bone morphogenetic protein: | 0.001 mg/ml |

These components are thoroughly blended while dry, and the balance of the composition mass is made up by addition of water, phosphate buffered saline, or any other physiologically acceptable liquid carrier. The composition may be packaged in this form or lyophilized for later reconstruction with water. The malleable properties of the composition are achieved by heating the composition to a temperature sufficient to exceed the liquefaction point of the gelatin, and then allowing the composition to cool to the temperature at which it gels.

REFERENCES

Cornell, C. *Techniques in Orthopaedics* 1992, 7, 55-63.
Bloebaum, R. D. *Human Bone Ingrowth and Mateaks*; Bloebaum, R. D., Ed.; Society for Biomaterials: Denver, Colo., 1996.
Einhorn, T. A. *Enhancement of Bone Repair Using Biomaterials*; Einhorn, T. A., Ed.; Society for Biomaterials: Denver, Colo., 1996.
Benedict, J. J. *The Role of Carrier Matrices on Bone Induction In Vivo*; Benedict, J. J., Ed.; Society for Biomaterials: Denver, Colo., 1996.
Strates, B.; Tiedeman, J. *European Journal of Experimental Musculoskeletal Research* 1993, 2, 61-67.
Urist, M. R. *Bone Morphogenetic Protein*; Urist, M. R., Ed.; W. B. Saunders Co.: Philadelphia, 1992, pp 70-83.
Yazdi, M.; Bernick, S.; Paule, W.; Nimni, M. *Clinical Orthopaedics and Related Research* 1991, 262, 281-285.
Younger, E.; Chapman, M. *Journal of Orthopaedic Trauma* 1989, 3, 192-195.
Hardin, C. K *Otolaringologic Clinics of North America* 1994, 27, 911-925.
A Senn, N. *The American Journal of the Medical Sciences* 1889, 98, 219-243.
Urist, M. R.; Huo, Y. K; Brownell, A. G.; Hohl, W. M.; Buyske, J.; Lietze, A.; Tempst, P.; Hunkapiller, M.; DeLange, R. J. *Procedures of the National Acadamy of Sciences, USA* 1984, 81, 371-375.
Urist, M. R.; Chang, J. J.; Lietze, A.; Huo, Y. K; Brownell, A. G.; DeLang, R. J. *Methods in Enzymology* 1987, 146, 294-313.
Lasa, C.; Hollinger, J.; Droham, W.; MacPhee, M. *Plastic and Reconstructive Surgery* 1995, 96, 1409-1417.
Nathan, R.; Bentz, H.; Armnstrong, R.; Piez, K; Smestad, T.; Elhingsworth, L.; McPherson, J.; Seyedin, S. *Journal of Orthopaedic Research* 1988, 6, 324-334.
Hench, L. L.; Andersson, O. H. *Bioactive Glasses*; Hench, L. L.; Andersson, O. H., Ed.; World Scientific Publishing Co. Pte. Ltd.: Singapore, 1993, pp 41-63.
Scarborough, N. *Bone Repair Using Allografts*; Scarborough, N., Ed.; Society for Biomaterials, 1996.
Frenkel, S. R.; Moskovich, R.; Spivak, J.; Zhang, Z. H.; Prewett, A. B. *Spine* 1993, 18, 1634-1639.
Sperling, L. H. *Introduction to Physical Polymer Science*; John Wiley and Sons, Inc.: New York, 1992.
McDonald, T. O.; Britton, B.; Borgmann, A. R.; Robb, C. A. *Toxicology* 1977, 7, 37-44.
Culling, C. F. A.; Allison, R. T.; Barr, W. T. *Cellular Pathology Technique;* 4 ed.;
Butterworths: London, 1985.
U.S. Pat. No. 5,481,601
U.S. Pat. No. 5,236,456
U.S. Pat. No. 5,405,390
U.S. Pat. No. 4,440,750
U.S. Pat. No. 4,394,370
U.S. Pat. No. 4,472,840
U.S. Pat. No. 4,678,470
WO 89/04646

The invention claimed is:

1. An implantable bone paste composition, for use in a recipient in need thereof, comprising a mixture of gelatin, osteogenic demineralized bone matrix (DBM) and, optionally, one or more additional substantially bioabsorbable, osteogenic components, wherein the optional osteogenic component is selected from the group consisting of:
bioactive glass ceramic, bioactive ceramic, calcium phosphate ceramic, hydroxyapatite, hydroxyapatite carbonate, corraline hydroxyapatite, calcined bone, tricalcium phosphate, bone morphogenetic protein, TGF-beta, PDGF, and mixtures thereof, and
wherein DBM is present at a concentration of from 24% (w/w) to 33% (w/w).

2. The composition of claim 1 wherein said composition gels at about 38° C.

3. The composition of claim 1, which is a frozen solution or is freeze-dried.

4. The composition of claim 1, wherein the demineralized bone matrix is in a powdered form, and is composed of particles in the size range between about 80-850µm in diameter.

5. An implantable bone paste composition, for use in a recipient in need thereof, consisting of a mixture of gelatin, osteogenic demineralized bone matrix (DBM), and optionally, a reconstitution solution, and/or one or more substantially bioabsorbable, osteogenic components, wherein the optional osteogenic component is selected from the group consisting of: bioactive glass ceramic, bioactive ceramic, calcium phosphate ceramic, hydroxyapatite, hydroxyapatite carbonate, corraline hydroxyapatite, calcined bone, tricalcium phosphate, bone morphogenetic protein, TGF-beta, PDGF, and mixtures thereof, and
wherein DBM is present at a concentration of from 24% (w/w) to 33% (w/w).

6. The composition of claim 1, wherein said gelatin is present at a concentration of from about 20% (w/w) to about 45% (w/w).

7. The composition of claim 1, comprising at least one osteogenic component selected from the group consisting of: bioactive glass ceramic, bioactive ceramic, calcium phosphate ceramic, hydroxyapatite, hydroxyapatite carbonate, corraline hydroxyapatite, calcined bone, tricalcium phosphate, bone morphogenetic protein, TGF-beta, PDGF, and mixtures thereof.

8. The composition of claim 7, comprising bioactive glass ceramic and/or bone morphogenetic protein.

9. The composition of claim 3, which is a frozen solution.

10. The composition of claim 3, which is freeze-dried.

11. The composition of claim 5, wherein said gelatin is present at a concentration of from about 20% (w/w) to about 45% (w/w).

12. The composition of claim 5, wherein the demineralized bone matrix is in a powdered form, and is composed of particles in the size range between about 80-850 µm in diameter.

13. The composition of claim 5, wherein said composition gels at about 38° C.

14. The composition of claim 5, which is a frozen solution.

15. The composition of claim 5, which is freeze-dried.

* * * * *

UNITED STATES PATENT AND TRADEMARK OFFICE
CERTIFICATE OF CORRECTION

PATENT NO. : 8,652,503 B2
APPLICATION NO. : 11/152548
DATED : February 18, 2014
INVENTOR(S) : John F. Wironen et al.

Page 1 of 1

It is certified that error appears in the above-identified patent and that said Letters Patent is hereby corrected as shown below:

In the Specification

Column 2,
Line 51, "inadequate for filing" should read --inadequate for filling--.

Column 15,
Line 7, "Mateaks;" should read --Materials;--.

Column 15,
Line 26, "A Senn, N." should read --Senn, N.--.

Column 15,
Line 37, "Armnstrong, R.;" should read --Armstrong, R.;--.

Column 15,
Line 38, "Elhingsworth, L, ;" should read --Ellingsworth, L.;--.

Signed and Sealed this
Third Day of June, 2014

Michelle K. Lee
*Deputy Director of the United States Patent and Trademark Office*